United States Patent [19]

Boebel et al.

[11] Patent Number: 4,538,594
[45] Date of Patent: Sep. 3, 1985

[54] RECTOSCOPE

[75] Inventors: Manfred Boebel, Oetischheim; Manfred Baier, Bretten-Diedelsheim; Gerhard Buess, Cologne, all of Fed. Rep. of Germany

[73] Assignee: Richard Wolf GmbH, Fed. Rep. of Germany

[21] Appl. No.: 555,155

[22] Filed: Nov. 25, 1983

[30] Foreign Application Priority Data

Nov. 26, 1982 [DE] Fed. Rep. of Germany ... 8233240[U]
May 26, 1983 [DE] Fed. Rep. of Germany ....... 3319049
Aug. 18, 1983 [DE] Fed. Rep. of Germany ....... 3329784

[51] Int. Cl.³ .............................. A61B 1/00
[52] U.S. Cl. ......................... 128/6; 128/340
[58] Field of Search ............. 128/4, 5, 6, 7, 8, 9, 128/10, 11, 303.19, 339, 340

[56] References Cited

U.S. PATENT DOCUMENTS

| 662,178 | 11/1900 | Truax | 128/340 |
| 1,127,948 | 2/1915 | Wappler | 128/7 |
| 2,236,842 | 4/1941 | Allyn | 128/6 |
| 2,691,370 | 10/1954 | Wallace | 128/6 |
| 2,990,830 | 7/1961 | Hett | 128/4 |
| 3,120,847 | 2/1964 | Cavaness | 128/340 |
| 3,675,641 | 7/1972 | Fiore | 128/6 |

Primary Examiner—William H. Grieb
Attorney, Agent, or Firm—Hill, Van Santen, Steadman & Simpson

[57] ABSTRACT

The rectoscope comprises a short, wide tube having a proximal coupling housing or a coupling housing which may be coupled at its distal side to a tube of optional length and width. The coupling housing may be coupled at its proximal side to a mandrel or an instrument carrier which is equipped with axially parallel through-bores, for sealed traversal by an optical system and auxiliary instruments. The tube is rigidly connected to an operating table or the like by means of a handle. Passages through which an inert gas may be introduced into the rectum under pressure lead into the rectoscope through the handle or separately. Vapors impeding the view which are developed in the rectal cavity during a coagulating operation may either be discharged direct into the atmosphere via a separate passage or retained in a reception vessel, together with quantities of fluid or body secretions drawn off by suction via a flushing and suction tube inserted into the rectal cavity, by means of a filter preconnected to a gas return pipe.

14 Claims, 17 Drawing Figures

RECTOSCOPE

BACKGROUND OF THE INVENTION

The invention relates to a rectoscope for examination of the rectum and for intestinal surgery.

To remove carcinomae or the like from the upper portion of the rectum, the procedure followed until now consisted for example in performing a resection of the coccyx or in wholly cutting through the anal sphincter, to enter the rectum. These methods implied on the one hand a comparatively protracted healing process and hospitalisation and, on the other hand, were also fraught with considerable risks.

The object of the invention consists in securing access to the rectum by means of a rectoscope without surgical interventions, whilst at the same time being able to make use of all auxiliary instruments needed for intestinal surgery under observation by means of an optical system.

SUMMARY OF THE INVENTION

For resolution of this problem, the rectoscope in accordance with the invention is characterised by a short, wide tube which may be connected proximally via a coupling housing and by means of an annular coupling to a mandrel expanding the sphincter to the diameter of the tube, or to an instrument carrier comprising axially parallel bores, and that the bores may have inserted in them in sealed manner an optical system, a needle holder and cylinders, lockable bayonet-fashion, of a sealing element, whereof the proximal extremities have joined to them gastight elastic extensions shut off proximally by a sealing cap through which extensions and the tube auxiliary instruments are insertible into the rectum inflatable by means of a gas.

By means of this solution, the sphincter may gradually be expanded and stretched to the diameter of the tube by means of the mandrel extending through the tube, so that the sphincter may thereupon receive the tube.

After withdrawing the mandrel, the instrument carrier is coupled to the tube proximally, after which it is possible to insert an optical system, a needle holder and sealing elements through the axially parallel bores of the instrument carrier, as well as to introduce all auxiliary instruments required into the rectum and to expand the rectum by means of an inert gas. The mandrel may be equipped with an axial passage which renders it possible for a rectoscope of conventional kind to be inserted for detection and subsequent preliminary examination of the area in question and for the subsequent insertion of the tube and mandrel to be performed in a positive and reliable manner.

It is advantageous to construct the coupling housing as a separate unit so that it may be coupled to tubes, including disposable tubes, of different lengths, thereby enabling adaptation to the depth of the area within the rectum which is to be examined.

The rectoscope substantially comprises either two components, namely the tube comprising the coupling housing as an unit, and the insertible instrument carrier, or advantageously three principal components, namely a tube, a coupling housing and an instrument carrier. In the latter case, rapid replacement of tubes and instrument carriers is possible, as well as easy cleansing and perfect sterilisation of all parts.

According to the invention, the distal extremity of the tube is lengthened at one side, and the optical system which is to be inserted extends through the tube along this lengthened side. Unobstructed vision is consequently always available for the optical system and the entire remanent space then allows of unimpeded intervention by means of the auxiliary instruments, which is no longer impeded by intestinal folds. The invention is described together with other advantageous and inventive features in the following, with reference to the drawings illustrating different embodiments, and in which:

DESCRIPTION OF THE PREFERRED EMBODIMENTS

According to the embodiment of FIGS. 1 to 5, the rectoscope comprises a short, wide tube 1 having a coupling housing 2 comprising an annular flange 1a and rotatable thereon a coupling ring 36 which co-operates in conventional manner with locking balls 2a (FIG. 5), which are situated in radial bores of the proximal annular flange 1a on the coupling housing 2 and may move into internal recesses in a peripheral portion of the coupling ring 36 upon release from the coupled position.

For insertion of the tube 1 into the rectum, a mandrel projecting distally out of the tube is passed through the tube, as will be described subsequently with reference to FIG. 11. The anal sphincter (constrictor muscle) is expanded by the mandrel to the width of the tube, so that the sphincter may thereupon receive the tube.

After withdrawal of the mandrel, the tube 1 has coupled to it an instrument carrier 3 which engages by its distal annular flange 4 in the annular flange 1a. so far that an annular groove 5 is situated in the area of the locking balls 2a which are caused by rotation of the coupling ring 36 to engage in this groove 5 and thus lock the instrument carrier 3 to the tube. The annular flange 4 has another annular groove wherein is inserted a sealing ring 6. The instrument carrier 3 is equipped with axially parallel bores 7 which in each case has a sealing ring 8 within an internal annular groove (FIG. 5) and may be arranged with identical spacing from the longitudinal axis, in regular mutual spacings or in an optional manner.

Figure 5:
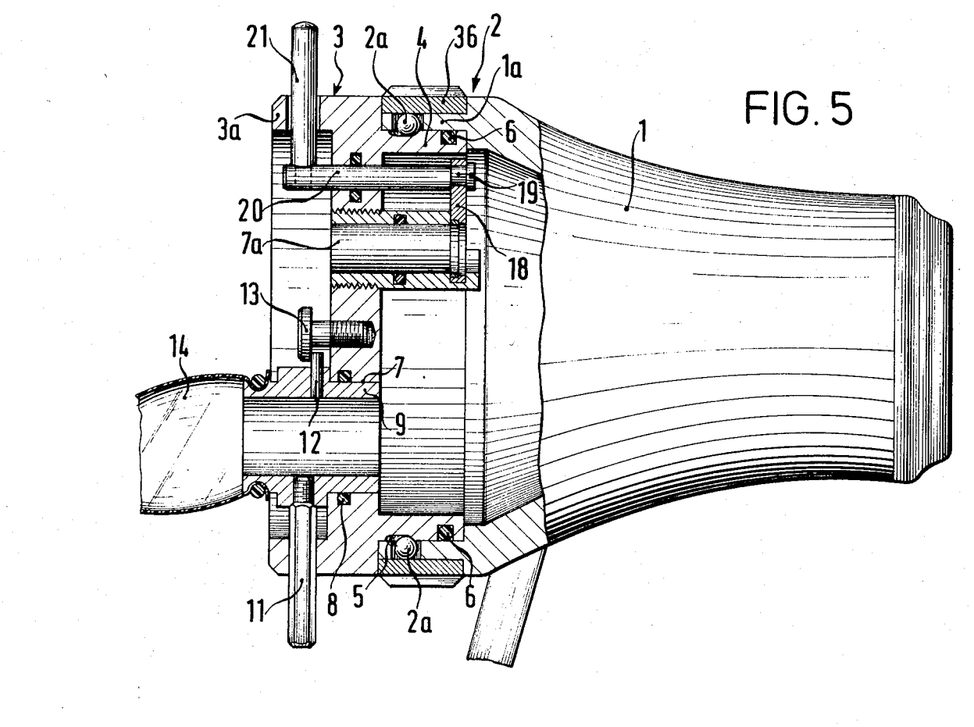
FIG. 5 is an enlarged axial cross-section of the instrument carrier coupled to the tube.

Short cylinders 9, sealed by means of sealing elements marked by the general reference number 10 (FIG. 3) may be inserted and locked in the bores 7 of the carrier 3. To this end, each cylinder 9 has a peg 11 which may be inserted into bayonet joint recesses in the proximal carrier ring flange 3a and rotated until a locking pin 12 passes behind the head or into a groove of a securing element 13, whereby the sealing element 10 is locked in a bore 7 (FIGS. 3 and 5).

The cylinder 9 of the sealing element 10 has joined to it a gas tight extension 14 of a highly elastic material, of which the proximal extremity is connected to a rotary member 15 and is shut off by means of a rubber cap 16 having a small central perforation. Auxiliary instruments of the nature required are passed through the sealing element 10 and the tube 1, and are sealed off as well as secured against dropping out by the closely fitting rim of the cap aperture 17, the auxiliary instruments being freely movable without hindrance within the rectal cavity by virtue of the elastic extension 14.

The optical system is passed through the inset sleeve 7a of the instrument carrier 3, and may be immobilised by means of clamping slide 18. This slide 18, which has a passage corresponding to the diameter of the optical system, is seated on an eccentric stud 19 on the extremity of an axially parallel spindle 20 which may be turned from the outside by means of a peg 21, so that the slide 18, traversed by the optical system, may describe a radial displacement and thereby grip the optical system (FIG. 5).

Figures 3, 4C:
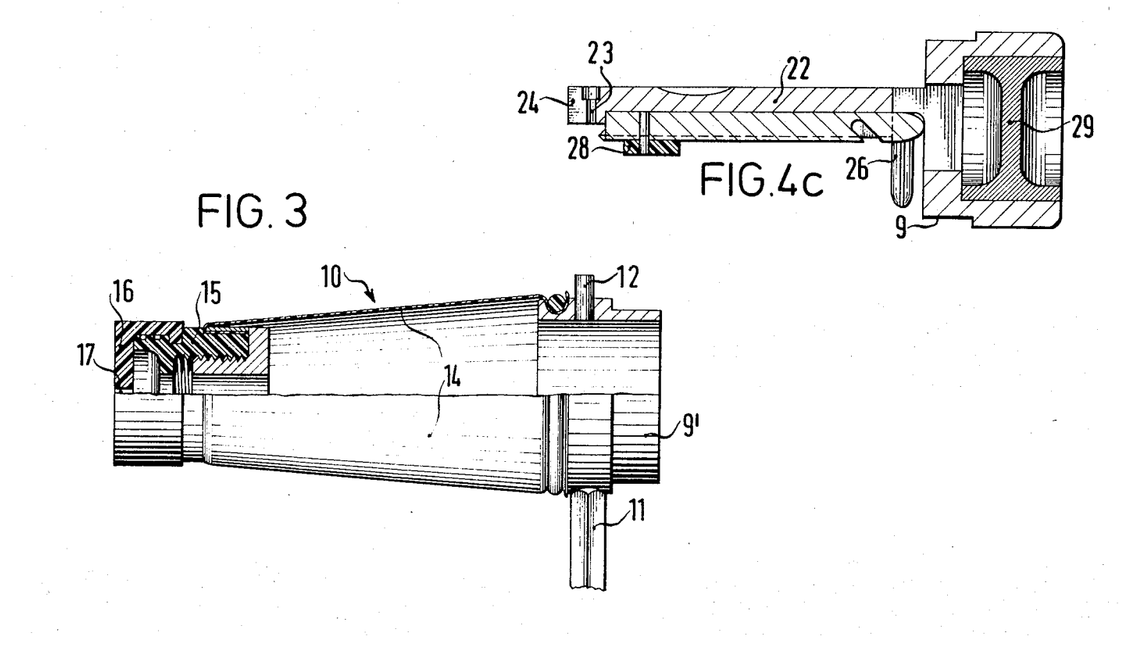
FIG. 3 is a side elevation with partial axial cross-sectioning of a sealing element intended to be connected to the instrument carrier.
FIGS. 4a, 4b and 4c are respectively a plan view, end view and axial cross-section along the line IV—IV of FIG. 4a of a needle holder.
Figure 4A:
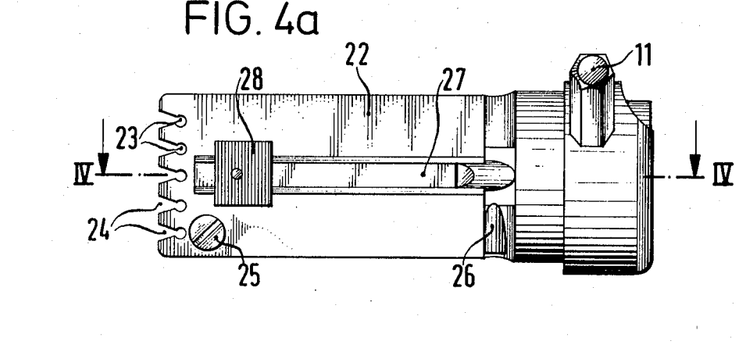
Figure 4B:
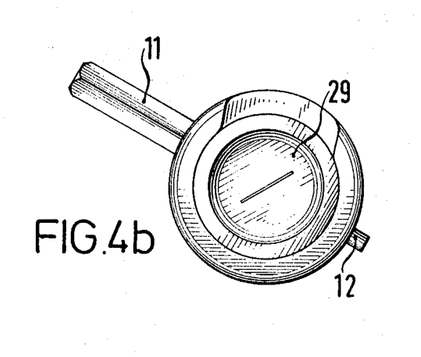

According to the invention, use may be made of all the other axially parallel bores 7 for reception of auxiliary instruments, one bore 7 also being able to receive a needle holder 22 according to FIGS. 4a, 4b and 4c, which may again be inserted into the bore 7, in a sealed manner, by means of its short cylinder 9. This needle holder 22 is required in the case of eradication of carcinomae of large area, causing large wounds, to allow of sewing up the wounds. The needle holder 22 receives the blunt end of the needles in cylindrical bores 23. These bores lead at the distal end into longitudinal V-shaped slots 24 extending throughout the end, so that the threads may be inserted at right angles to the end through the longitudinal slots 24 into the bores 23 and the needles may be inserted with their blunt extremities into the upper diametrically enlarged part of the bores 23. Each thread is then led downwards out of the bore 23, around the guiding pin 25 and outwards, and thereupon inwards again around the guiding element 26 over the entire width of the needle holder 10. By means of a known thread guide which at its front extremity has a V-shaped excision, distally directed obliquely with respect to the axis, the thread is picked up and led out of the seal 29 by axial displacement of the thread guide by means of the handle 28 connected thereto.

To establish operating conditions which are as constant as possible for intervention in the rectum, the tube 1 is connected to a handle 30 which has a passage for insufflation of an inert gas into the rectal cavity which is to be expanded, said passage being equipped with a cock 31 for interruption of the gas supply. The handle 30 is equipped with a device 32 for fastening on the operating table or on a support member, to secure the position of the tube.

Figure 1:
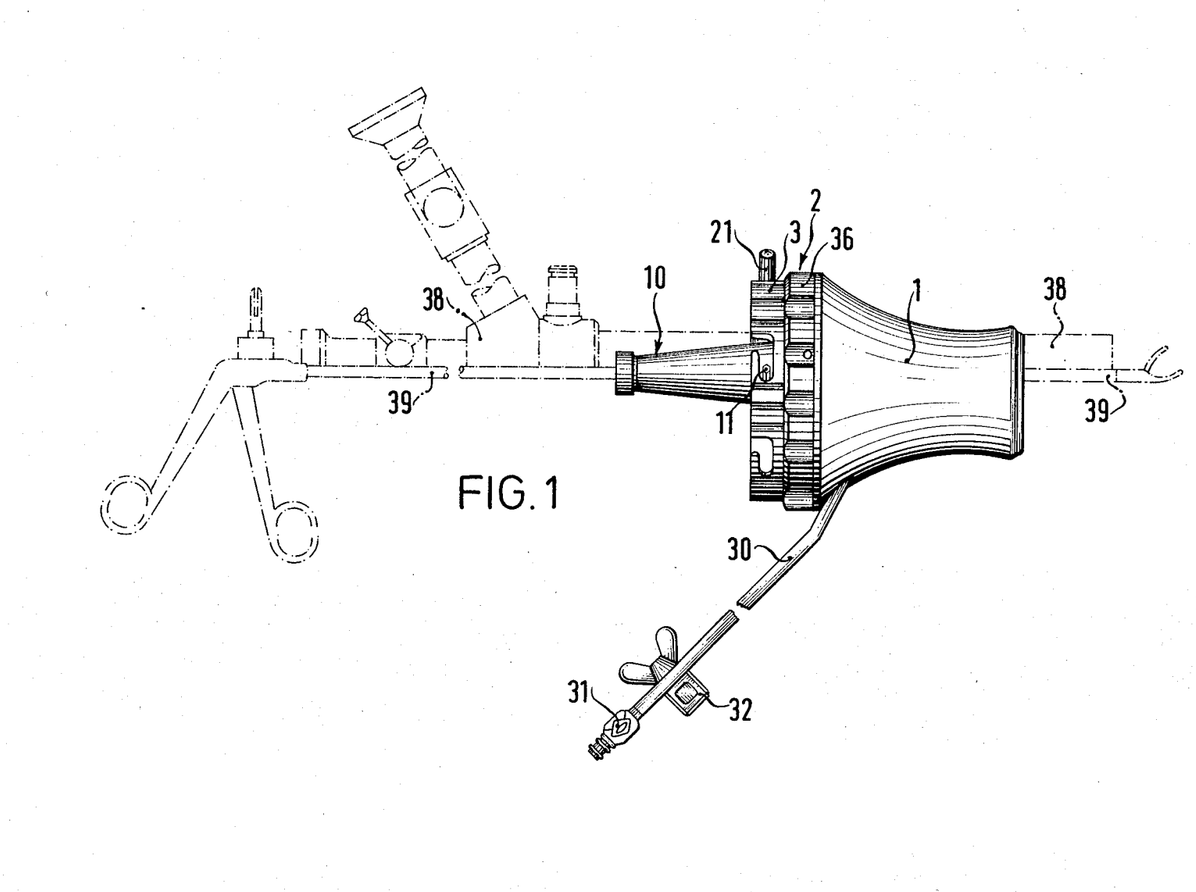
FIG. 1 is a first embodiment of a rectoscope in accordance with the invention, with a laparoscope and an auxiliary instrument shown in dotted lines.
Figure 2A:
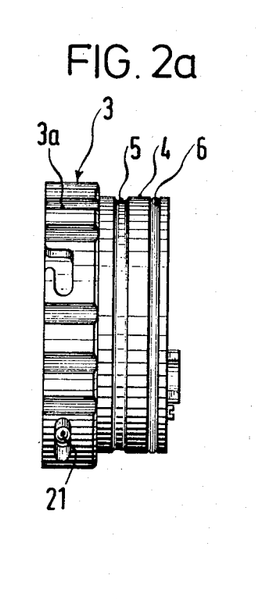
FIG. 2a is an enlarged side elevation of the instrument carrier.
Figure 2B:
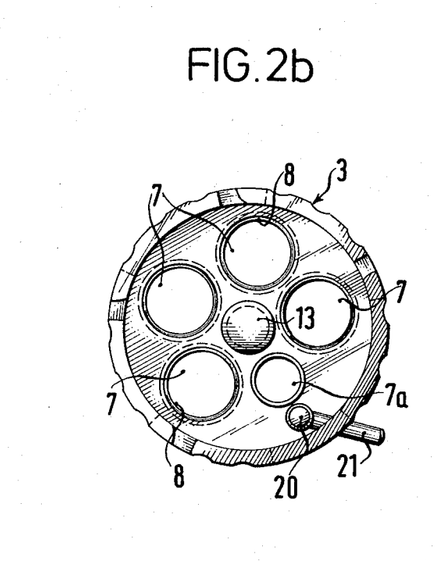
FIG. 2b is the proximal end of the instrument carrier.
Figure 2C:
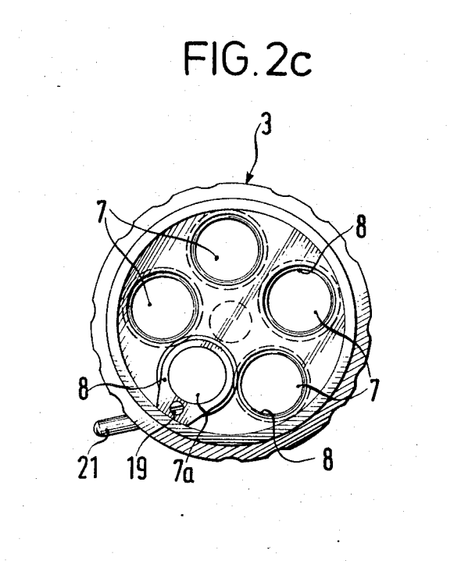
FIG. 2c is the distal end of the instrument carrier.

According to the second embodiment of FIGS. 6 to 11, in which parts corresponding to those of FIGS. 1 to 5 bear the same reference numbers, the rectoscope comprises three essential parts, namely the wide tube 1 which is lengthed in comparison with FIG. 1 and is equipped at the distal extremity with an annular elastic protector 1a preventing injuries within the rectum, a separate coupling housing 2 and an instrument carrier 3 as described with reference to FIGS. 1, 2, 3 and 5.

The tube 1 is connected in interchangeable manner with tubes of different length to the coupling housing 2. To this end, the tube 1 has proximally, for example, two diametrically opposed external segments 32 which may be engaged in two recesses 33 in a distal annular flange 34, which has an outer screw-thread, of the coupling housing, thereby preventing rotation of the parts 1 and 2 with respect to one another. The coupling of the parts 1 and 2 is then performed by means of a screw ring 35 which is screwed on to the annular flange 34 with its radial flange engaging against the distal extremities of the segments 32, either directly or via a complementary spring. The tube 1 is thereby sealed to the coupling housing 2 by means of an interposed sealing ring 2a. Other joints are also possible between the tubes 1 and the coupling housing 2, e.g. bayonet-type joints.

The insertible instrument carrier 3 is locked in the coupling case 2 by means of an outer coupling ring 36 comprising a handle 36a (FIG. 6), the annular flange 3a of the carrier 3 sealing against the coupling housing 2 by means of a sealing ring 37, the rotatable coupling ring 36 co-operating with locking balls via impingement surfaces. Other locking means are also possible, e.g. a bayonet-type locking device.

Figure 6:
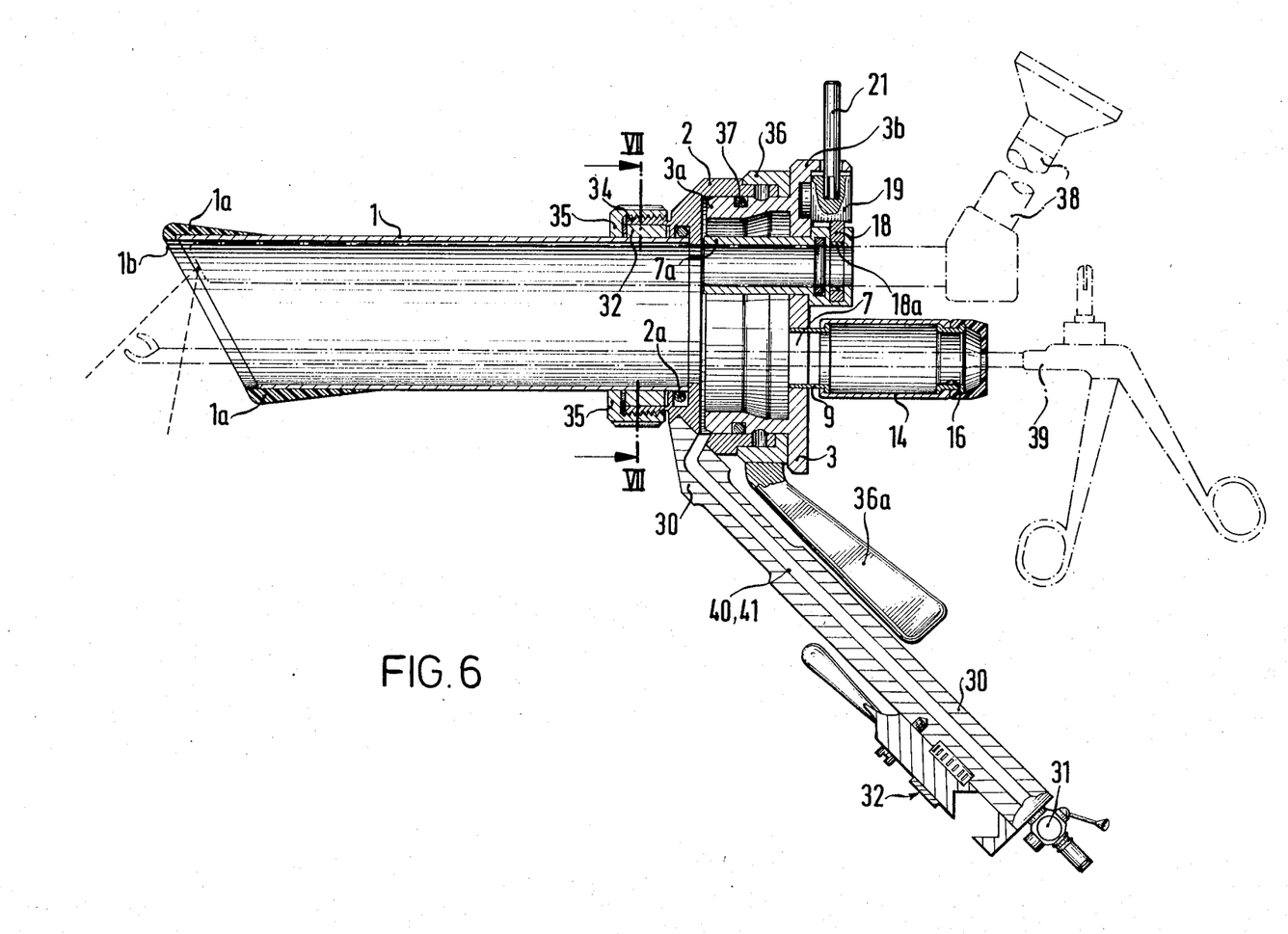
FIG. 6 is a second embodiment of a rectoscope in accordance with the invention in axial cross-section.

The instrument carrier 3 is equipped with a passage in the form of a cylindrical sleeve 7a which is intended for traversal by the optical system 38 (shown in broken lines) and sealed against the carrier 3 by means of a sealing ring, and with passages 7 for traversal by auxiliary instruments 39 (FIG. 6). To this end, the optical system 38 extends through the tube 1 internally and along the longest tube side extended at one side by the termination 1b. It is also possible however to turn the instrument carrier 3 after freeing the ring 36 to obtain a modified position of the optical system and of the auxiliary instruments, if this becomes necessary for examination and for implementing interventions, without completely separating the connection between the instrument carrier and coupling element, and without loss of gas.

At the proximal side, the instrument carrier 3 has a flange 3b occupying no more than a part of the periphery and having a radial slot for a pin 21 of an eccentric 19 whereby a slide 18 having a plastics material insert 18a therein are moved in contact against the optical system, which is thereby immobilised.

For traversal by auxiliary instruments, the passages 7 of the instrument carrier 3 are followed by short angled lead-ins 9 (FIGS. 3 and 8) comprising external proximal collars over which it is possible in each case to secure a highly flexible extension 14 whereof the proximal extremity has a rotary member 15 and a terminal sealing cap 16 comprising a narrow perforation 17 providing a sealed lead-in for the auxiliary instruments 39. The auxiliary instruments may be passed to the area of operation through the rectoscope without limitations regarding their displacement, through the lead-ins 9 aligned at an angle obliquely to the distal centre. (FIG. 8).

To secure a stable position of the rectoscope during examination and during the interventions, the coupling housing 2 is connected to a support 30 which is to be fastened to an operating table. This support 30 is traversed by two passages 40, 41, which on the one hand open into the coupling housing 2 and are equipped at the other extremity with closable connectors 31 for the introduction of an inert gas.

Figure 9:
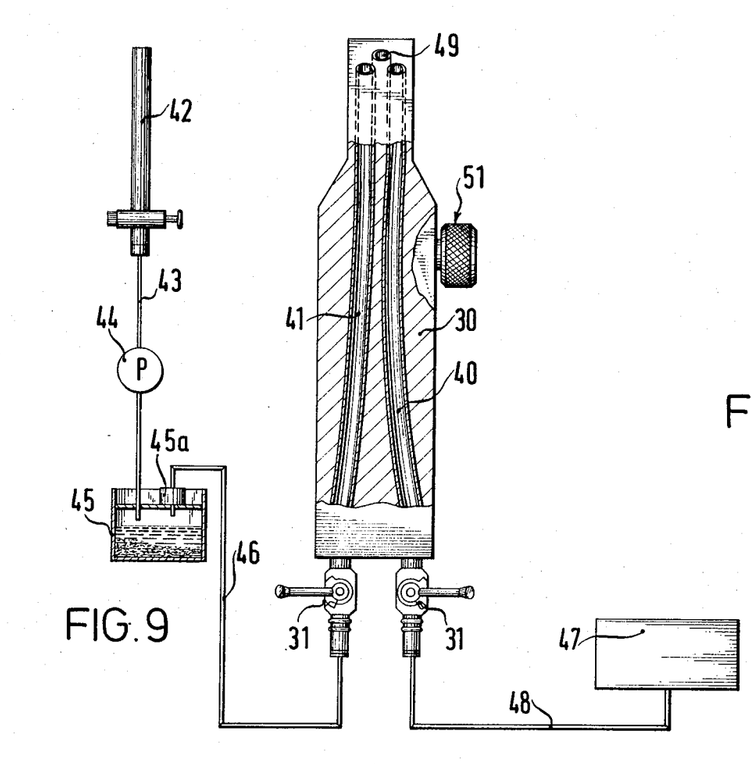
FIG. 9 is a view of the handle of the rectoscope and diagrammatically illustrates the delivery and discharge passages.
Figure 10:
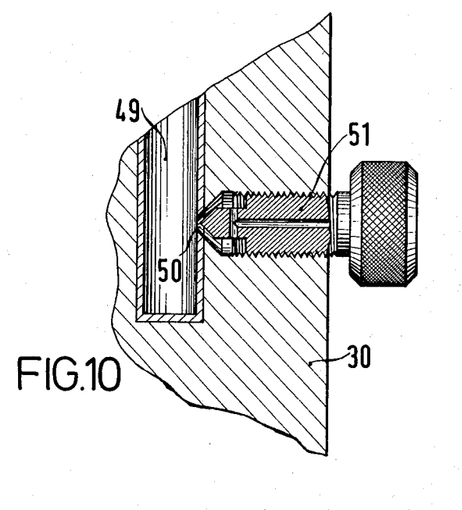
FIG. 10 is an enlarged partial cross-section through the handle comprising a derivation passage and adjustable valve.

To this end, gas is supplied to the body cavity for expansion purposes by means of the pneumatic device 47 via a connector 31 and the passage 40/41 (FIG. 9).

Blood, secretions or the like may be drawn off by suction during the intervention in the body cavity via a suction hose 43 and a suction tube 42 inserted through the instrument carrier 3 and the tube 1, by means of a pump 44, and into a closed reception vessel 45. Since gas is also entrained by suction to the vessel 45 from the body cavity, this volume should be restored to the body cavity from the vessel 45 complementarily by means of the pump 44 or of another pump, via the duct 46 and the passage 41.

It is also possible however, to proceed in such manner as to post-connect a filter 45a which retains smoke and vapours to the vessel 45, while the gas stripped of these may return direct into the body cavity.

Another possibility of eliminating smoke or vapours engendered, for example, upon performing a coagulation from the rectum cavity, consists in ducting these or the gas contaminated by these within the body cavity direct into the atmosphere via a separate passage 49, to which end it is advantageous to limit this gas flow by means of a restrictor or adjustable valve 51, in such manner that the pressure within the rectal cavity may be maintained by means of the pneumatic device 47.

Figure 6A:
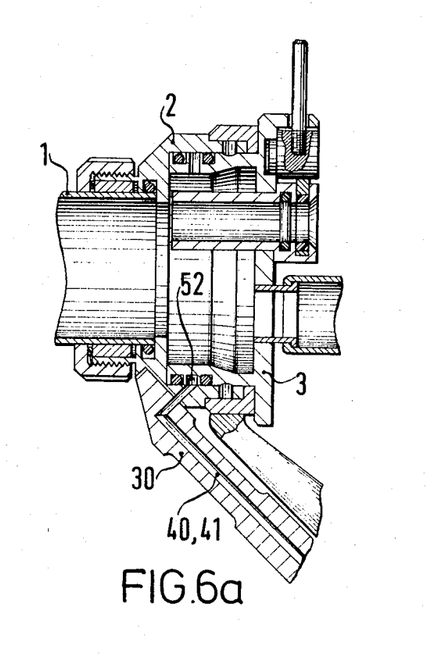
FIGS. 6a, 6b show the coupling case and instrument carrier according to FIG. 6 in axial cross-section with differently organised passages for delivery into and discharge of gases from the rectum.
Figure 6B:
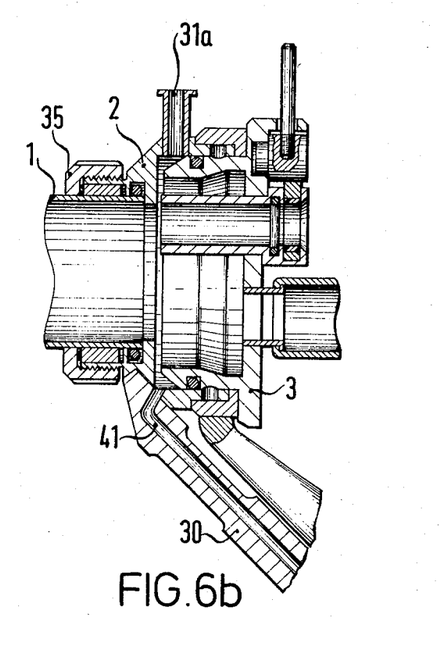

The case may arise in which the proximal section of the rectoscope is held lower by the surgeon than the remanent section, so that fluids may then pass from the rectum and via the rectoscope into the passages 40, 41 and possibly into the passage 49. For this reason, it is advantageous for the passages (FIG. 6a) to lead into the rectoscope at the top via a peripheral groove 52 or if need be via several peripheral grooves in the axial flange of the carrier 3, or for the connector 31 to lead into the rectoscope at the top via a stub pipe 31a, as shown in FIG. 6b, instead of into the handle 30.

Figures 7, 8, 11:
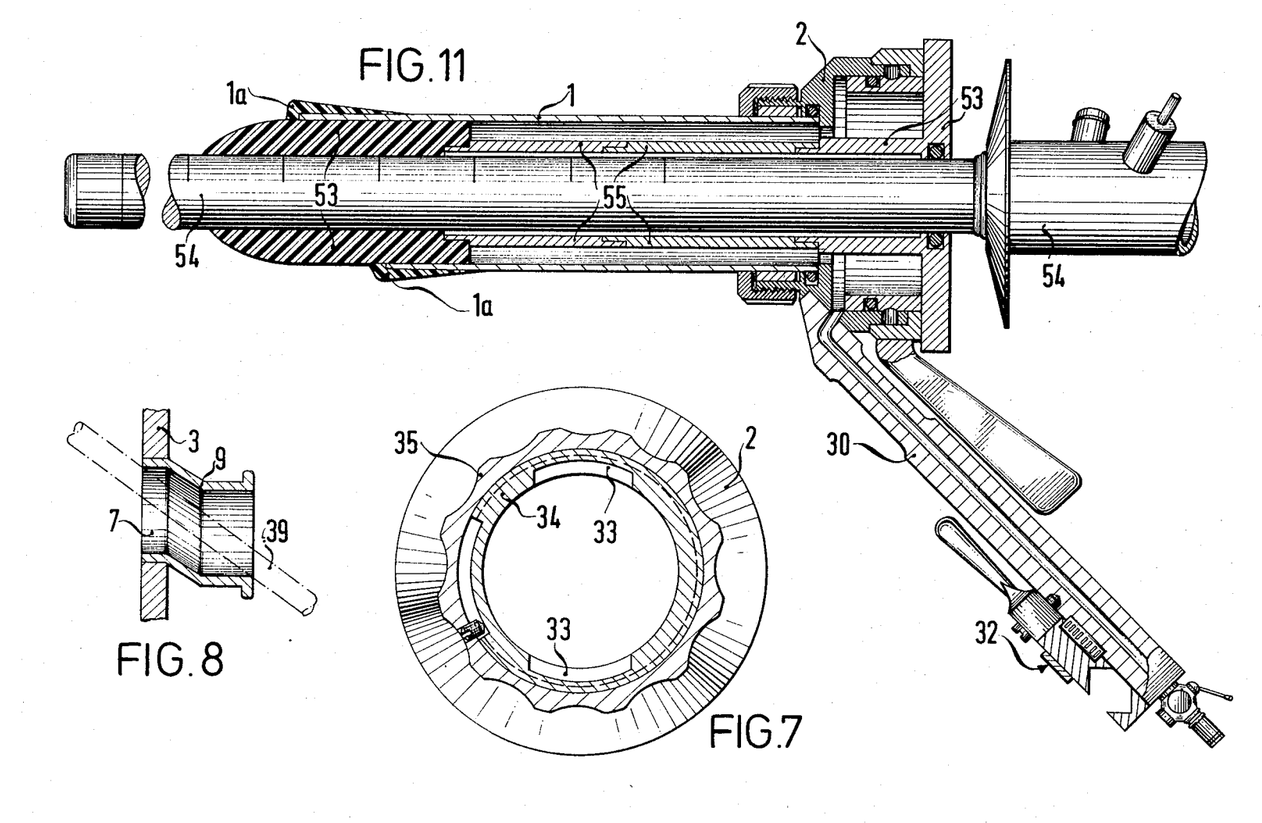
FIG. 7 is a cross-section along the line VII—VII of FIG. 6.
FIG. 8 is a partial cross-section of an instrument lead-in of the instrument carrier according to FIG. 6.
FIG. 11 is an axial cross-section through the tube and through a mandrel passed through the tube.

As already stated, the insertion of the tube 1 into the rectoscope via the sphincter is performed by virtue of the fact that, according to FIG. 11, the tube 1 is traversed by a mandrel 53 which has an axial passage for traversal by a rectoscope 54. This mandrel 53 enlarges, from the distal extremity to the tube extremity, to the diameter of the tube 1. This mandrel 53 may be varied in length by means of cylindrical sleeves 55 which may be screwed together, for adapting to the tube length, and is connected to the coupling housing at the proximal side.

We claim:

1. Rectoscope for examination of the rectum and for intestinal surgery, comprising a short, wide tube equipped proximally with a coupling housing having means for connecting selectively to a mandrel for expanding the sphincter to the diameter of the tube and to an instrument carrier comprising axially parallel bores, an optical system for insertion into one of the bores and a needle holder and a sealing element for insertion into another of the bores, means for sealing said optical system, needle holder and sealing element in its associated bore, said sealing element comprising a cylinder portion associated with means for locking it, bayonet-fashion in a bore, said cylinder portion having joined to its proximal extremity a gas tight elastic extension which is closed off proximally by a sealing cap, auxiliary instruments being insertible through said extension and the tube into the rectum which may be inflated by means of a gas.

2. Rectoscope according to claim 1, characterised in that the mandrel which serves for inserting the tube into the rectum via the sphincter and is coupled proximally with the coupling housing has a longitudinally extending passage for traversal by a rectoscope shaft and is adaptable in length to different tube lengths by cylindrical sleeves which may be assembled end-to-end by screw-threads.

3. Rectoscope according to claim 1, characterised in that the coupling housing forms a unit separate from the tube of the rectoscope and may be coupled distally to wide tubes of different length and width and proximally to the mandrel and the instrument carrier.

4. Rectoscope according to claim 1, characterised in that the coupling housing is equipped with a handle having means defining several closable passages extending therethrough and connecting to the tube for supply of inert gas from a gas source into the rectum and for discharge of smoke and vapours from the rectum, and that the handle is equipped with a clamping device for fastening to a support.

5. Rectoscope according to claim 1, characterised in that the distal tube extremity is extended at one side and that the optical system guided by the tube extends along said extended side.

6. Rectoscope according to claim 1, characterised in that the mandrel and the instrument carrier engage in sealed manner with an annular flange of the coupling housing and may be joined to the coupling case by means of a manually rotatable ring of the coupling.

7. Rectoscope according to claim 6, characterised in that the instrument carrier is equipped with a peripheral flange of part-annular form at the proximal side, which is traversed by an outwardly directed handle of an eccentric for locking the optical system in its bore of the instrument carrier.

8. Rectoscope according to claim 1, characterised in that several angled short cylinders intended to be traversed by auxiliary instruments are secured in the bores of the instrument carrier, said short cylinders having proximal outer peripheral collars over which may be fitted in each case a highly flexible extension having an elastic closure cap comprising a passage opening through which an auxiliary instrument may be passed in sealed manner.

9. Rectoscope according to claim 4, characterised by a suction tube which may be inserted in sealed manner into the body cavity via a bore of the instrument carrier and the tube, and is connected via a hose and a pump to a closed reception vessel from which gas drawn off by suction from the body cavity may be returned into the body cavity via the pump, an additional pump or directly, by-passing the pump, via a hose and one of the passages through the handle.

10. Rectoscope according to claim 4, characterised by means defining a third passage in the handle, which opens to the atmosphere via a restrictor or an adjustable valve, and is in communication with the rectum via the tube connected to the coupling housing.

11. Rectoscope according to claim 9, characterised in that a filter intended to filter out smoke and vapours coming from the rectum is interposed in the duct between the reception vessel and the passage through the handle leading into the coupling housing.

12. Rectoscope according to claim 4, characterised in that the passages in the upper part of the instrument carrier open into the rectoscope via at least one annular groove or connector pipe of the coupling housing.

13. Rectoscope according to claim 1, characterised in that a hermetically insertible needle holder for reception of several surgical needles is provided for one of the axially parallel bores of the instrument carrier, the threads being led out through a seal with its thread guide known per se, by means of an axially displaceable handle.

14. Rectoscope according to claim 13, characterised in that the needles have their distal extremities engaged without contact in recesses and are releasably secured with their blunt extremities in diametrically enlarged parts of limited depth of bores into which open slots which diverge outwardly in V-form in the axial direction extend throughout the length of the bores.

* * * * *